United States Patent [19]

Yamada et al.

[11] Patent Number: 5,043,271
[45] Date of Patent: Aug. 27, 1991

[54] DNA ENCODING RABBIT TNF, VECTOR HAVING SAID DNA INSERTED THEREINTO, HOST TRANSFORMED WITH SAID VECTOR, RABBIT TNF POLYPEPTIDE, AND PROCESS FOR PRODUCTION THEREOF

[75] Inventors: Masaaki Yamada, Kyoto; Yasuji Furutani, Toyonaka; Nitsue Notake, Suita, all of Japan

[73] Assignee: Dainippon Pharmaceutical Co., Ltd., Osaka, Japan

[21] Appl. No.: 677,680

[22] Filed: Nov. 30, 1984

[30] Foreign Application Priority Data

Dec. 2, 1983 [JP] Japan ............................. 58-228790

[51] Int. Cl.$^5$ ...................... C12P 21/00; C12N 15/00; C12N 1/20; C07H 10/12
[52] U.S. Cl. .......................... 435/69.5; 435/172.3; 435/320.1; 435/252.3; 435/252.33; 435/91; 435/255; 435/240.1; 435/240.2; 435/240.4; 536/27; 935/73; 935/62; 935/60; 935/27; 935/11; 935/21
[58] Field of Search ............... 435/68, 172.3, 240, 435/241, 91, 253, 317, 255, 320, 320.1, 252.33, 240.2, 240.1, 240.4, 69.5; 260/112 R, 112 B, 112.5 R; 935/9, 11, 13, 27, 29, 56, 62, 73, 60; 514/12; 537/27

[56] References Cited

U.S. PATENT DOCUMENTS 4,529,594 7/1985 Hayashi et al. ...................... 514/12
4,879,226 11/1989 Wallace et al. ..................... 435/69.6

OTHER PUBLICATIONS

Ruff et al., *J. Immunology*, vol. 125(4), Oct. 1980, pp. 1671–1677, "Purification and Physio-Chemical Characterization of Rabbit Tumor Necrosis Factor".
Matthews et al., *Br. J. Cancer*, vol. 42, pp. 416–422, 1980, "Tumor Necrosis Factor from the Rabbit, IV, Purification and Chemical Characterization".
Matthews et al., *Br. J. Cancer*, vol. 38, 1978, pp. 302–304, "Tumor Necrosis Factor from the Rabbit, I, Mode of Action, Specificity and Physiochemical Properties".
Matthews, *Br. J. Cancer*, vol. 44, pp. 418–424, 1981, "Tumor-Necrosis Factor from the Rabbit, V, Synthesis In Vitro by Mononuclear Phagocytes from Various Tissues of Normal and BCG-Injected Rabbits".

*Primary Examiner*—Robin L. Teskin
*Attorney, Agent, or Firm*—Wenderoth, Lind & Ponack

[57] ABSTRACT

A novel cloned DNA encoding a rabbit Tumor Necrosis Factor (TNF) or a principal portion thereof, a vector having said DNA inserted thereinto, a host transformed with said vector, a novel polypeptide having or containing the rabbit TNF or a principal portion thereof, and a process for producing said polypeptide comprising cultivating said transformed host.

38 Claims, 4 Drawing Sheets

DNA ENCODING RABBIT TNF, VECTOR HAVING SAID DNA INSERTED THEREINTO, HOST TRANSFORMED WITH SAID VECTOR, RABBIT TNF POLYPEPTIDE, AND PROCESS FOR PRODUCTION THEREOF

This invention relates to a cloned DNA encoding a rabbit Tumor Necrosis Factor (simply TNF hereinafter) or a principal portion thereof, a vector having said DNA inserted thereinto, a host transformed with said vector, a process for producing a polypeptide having or containing a rabbit TNF or a principal portion thereof by cultivating said host, and to a polypeptide having or containing a rabbit TNF or a principal portion thereof produced by said process.

The present invention also pertains to a DNA having or containing a base sequence corresponding to the amino acid sequence of a rabbit TNF or a principal portion thereof or an amino acid sequence resulting from modification of part of said amino acid sequence, a vector having said DNA inserted thereinto, a host transformed with said vector, a polypeptide produced from said host which has the amino acid sequence of a rabbit TNF or a biological activity substantially equivalent thereto and immunologically crosses with it, and to processes for production thereof.

Carswell et al. found that the serum of mice infected with bacillus Calmette-Guérin (BCG) and then treated with an endotoxin contains a substance which necrotizes transplanted Meth A sarcoma; and named it a tumor necrosis factor (TNF) [Proc. Nat. Acad. Sci., USA, 72, 3666 (1975)].

TNF is considered to be a physiologically active substance released from macrophages, and is known to be characterized in that (i) when it is administered to animals bearing a certain kind of tumor (for example, Meth A sarcoma), it induces necrosis of the tumor and cures the animals; (ii) it has a cytotoxic effect in vitro on a certain kind of tumor cell (such as L cells which are mouse tumor cells, and PC-10 cells derived from human tumor) but has scarcely any injurious effect on normal cells; and (iii) its activity is not animal species-specific.

Because of these characteristics, it has been strongly desired to develop TNF as a new type of antitumor agent.

TNF or a TNF-like substance has been reported in the following literature references or published in the following patent documents.
Green et al., Proc. Nat. Acad. Sci., USA, 73, 381 (1976).
Matthews et al., Br. J. Cancer, 42, 416 (1980).
Ruff et al., J. Immunol., 125, 1671 (1980).
Mannel et al., Infect. Immunity, 28, 204 (1980).
Haranaka et al., Japan. J. Exp. Med., 51, 191 (1981).
European Patent Publication No. 90892.
European Patent Publication No. 86475.
Japanese Patent Publication No. 21621/1983.

The processes disclosed in these documents are characterized by involving purification of TNF from body fluids (e.g., blood) or tissues of rabbits, mice, hamsters or guinea pigs as raw materials. The products, however, are not so clearly defined, and it is evident that various restrictions are imposed on these processes in regard to the supply of raw materials and the purities of the final products.

The present inventors have made various investigations with an eye on the application of recombinant DNA technology. These investigations have led to successful cloning of DNA encoding a rabbit TNF and elucidation of what the rabbit TNF is.

More specifically, the present inventors cultivated rabbit macrophages in vitro together with suitable inducers, and ascertained that the rabbit TNF was produced and released in the culture medium. Subsequently, the present inventors found cultivation conditions which caused the rabbit TNF mRNA to be produced and accumulated in high concentrations in the macrophages. The present inventors further succeeded in cloning cDNAs encoding the TNF and determined their base sequences. Furthermore, the present inventors succeeded in producing polypeptides having or containing the TNF in a host transformed with an expression vector having the cloned cDNA inserted thereinto. In the course of these investigations, the present inventors also found that the TNF is formed as a precursor.

A typical DNA in accordance with this invention which encodes rabbit TNF or its principal portion is represented by a base sequence of the following formula [I]

(5')-TCA GCT TCT CGG GCC CTG AGT GAC AAG  [I]
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3').

The DNA having a base sequence represented by formula [I] above encodes a polypeptide represented by the following formula [A]

Ser Ala Ser Arg Ala Leu Ser Asp Lys Pro  [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.

It has been found that the DNA encoding rabbit TNF in accordance with this invention assumes a precursor structure and the precursor is encoded in a DNA having a base sequence represented by the following formula [II] or a DNA resulting from the addition of ATG to its 5'-terminal.

(5')-AGC ACT GAG AGT ATG ATC CGG GAC GTC  [II]
GAG CTG GCG GAG GGG CCG CTC CCC AAG AAG
GCA GGG GGG CCC CAG GGC TCC AAG CGC TGC
CTC TGC CTC AGC CTC TTC TCT TTC CTG CTC

-continued
```
GTG GCT GGA GCC ACC ACG CTC TTC TGC CTG
CTG CAC TTC AGG GTG ATC GGC CCT CAG GAG
GAA GAG CAG TCC CCA AAC AAC CTC CAT CTA
GTC AAC CCT GTG GCC CAG ATG GTC ACC CTC
AGA TCA GCT TCT CGG GCC CTG AGT GAC AAG
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3').
```

The DNA having the above base sequence of formula [II] encodes a polypeptide represented by the following formula [B]

```
Ser Thr Glu Ser Met Ile Arg Asp Val Glu           [B]
Leu Ala Glu Gly Pro Leu Pro Lys Lys Ala
Gly Gly Pro Gln Gly Ser Lys Arg Cys Leu
Cys Leu Ser Leu Phe Ser Phe Leu Leu Val
Ala Gly Ala Thr Thr Leu Phe Cys Leu Leu
His Phe Arg Val Ile Gly Pro Gln Glu Glu
Glu Gln Ser Pro Asn Asn Leu His Leu Val
Asn Pro Val Ala Gln Met Val Thr Leu Arg
Ser Ala Ser Arg Ala Leu Ser Asp Lys Pro
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.
```

It should be understood that the DNA of this invention encoding a rabbit TNF polypeptide or its principal portion includes DNAs having or containing a base sequence represented by formula [I] or [II], DNAs resulting from partial modification thereof, and allelic mutants thereof. Accordingly, these DNAs are generically referred to hereinafter as the "DNA of this invention". It should be understood further that polypeptides produced by hosts transformed by expression vectors having the aforesaid DNAs inserted thereinto, or degradation products thereof are included within the polypeptide of this invention so long as they show biological activities substantially equivalent to rabbit TNF polypeptide and immunologically cross with the TNF polypeptide. Hereinafter, such polypeptides are generically referred to as the "polypeptide of this invention".

The partially modified DNAs mentioned above mean DNAs having a base sequence corresponding to formula [I] or [II] in which one or more codons are deleted, and/or one or more codons are substituted by one or more other codons.

Processes for the preparation of the DNA of this invention and the polypeptide of this invention will be described in detail.

The DNA of this invention encoding rabbit TNF or a principal portion thereof can be produced by cultivating rabbit macrophages together with inducers, separating a fraction containing rabbit TNF mRNA from the macrophages, preparing a cDNA library from the fraction, and cloning the rabbit TNF cDNA by using a differential hybridization method followed by mRNA hybridization translation assay.

Furthermore, according to this invention, it is possible to cultivate in a suitable culture medium a host transformed with an expression vector containing DNA derived from the rabbit TNF cDNA and obtain a polypeptide having or containing rabbit TNF or a principal portion thereof from the host cells or the culture medium.

As stated above, the DNA having or containing the DNA encoding the rabbit TNF or a principal portion thereof can be modified by techniques known per se to form a partially modified DNA having or containing a base sequence corresponding to formula [I] or [II] in which (A) one or more codons are deleted, and/or (B) one or more codons are substituted by one or more other codons.

In the above DNA or its modified DNA of this invention, one or more codons can be substituted by a corresponding degenerated codon or codons.

Thus, according to this invention, a cloned DNA having or containing a base sequence encoding a rabbit TNF polypeptide or a principal portion thereof or a modified DNA thereof can be produced by A. cultivating rabbit macrophages together with inducers,
B. separating a fraction containing rabbit TNF mRNA from the macrophages,
C. preparing a single-stranded cDNA (sscDNA) from the mRNA by using reverse transcriptase and then converting it to a double-stranded cDNA (dscDNA),
D. inserting the dscDNA into a vector,
E. introducing the recombinant plasmid into a host to transform it and construct a cDNA library,
F. cloning cDNA encoding the rabbit TNF or its principal portion from the library by using a differential hybridization method followed by mRNA hybridization translation assay, and
G. as desired, partially modifying the cloned cDNA.

A polypeptide having or containing rabbit TNF or a principal portion thereof can be produced by inserting the resulting DNA into an expression vector, transforming a host with the vector, and cultivating the transformed host.

Now, the process for producing the DNA of this invention and the process for producing the polypeptide of this invention will be described in detail. It should be understood however that the operations and conditions in the individual steps of the processes to be described hereinbelow are well known in the art, and the processes of this invention are never limited to these specific processes to be described below.

[I] Production of cloned DNA of the invention

I-1. Preparation of rabbit TNF mRNA

According to this invention, the rabbit TNF mRNA can be obtained, for example, by the following method.

Rabbits are intravenously or intraperitoneally injected with an activator of the reticuloendothelial system, such as *Propionibacterium acne*, BCG or Zymosan, and killed 7 to 14 days after the injection. Macrophages are obtained from the alveolus, abdomen, blood or other tissues of the animals. The macrophages are seeded in a dish at a cell density of about $2 \times 10^4$ to $1 \times 10^6$ cells per cm$^2$, and pre-cultivated at 35° to 38° C., preferably about 37° C. and a humidity of about 90 to 100% in air containing about 5 to 10% of carbon dioxide for about 30 minutes to about 2 hours. Then, an endotoxin obtained from a gram-negative bacterium, preferably lipopolysaccharides derived from *Escherichia coli, Pseudomonas aeruginosa* or *Salmonella typhi*, is added as an inducer, and cycloheximide is added as a protein synthesis inhibitor. The cultivation is continued further for 3 to 8 hours to accumulate rabbit TNF mRNA in the macrophages. The pre-cultivation may be omitted. The amount of the endotoxin is generally about 0.1 to 1000 micrograms/ml (final concentration; the same hereinbelow), preferably about 1 to 100 micrograms/ml. At this time, a phorbol ester such as phorbol-12-myristate-13-acetate, phorbol-12,13-didecanoate and phorbol-12,13-dibenzoate may be further added as an inducer in an amount of about 1 to 2000 ng/ml. The amount of the protein synthesis inhibitor varies depending upon its type. For example, in the case of cycloheximide, it is 0.1 to 50 micrograms/ml. Various culture media suitable for the cultivation of mammalian cells can be used as the culture medium. Examples include RPMI-1640, Eagle's MEM medium, and Dulbecco's modified MEM medium [for the compositions of the above media, see, for example, "Cell Cultivation Manual" edited by Y. Sohmura, Kodansha (1982), and J. Paul "Cell and Tissue Culture", E. & S. Livingstone Ltd. (1970)]. Preferably, an animal serum (such as fetal bovine serum or calf serum) is added to the culture medium in an amount of about 1 to 20%.

After the cultivation, total RNA is extracted from the cells by a customary method, for example the method of Chirgwin et al. [Biochemistry, 18, 5294 (1979)], and then by affinity column chromatography on oligo(dT)cellulose or poly(U)Sepharose or by a batch method, a fraction containing poly(A)mRNA is separated. An enriched mRNA fraction with rabbit TNF mRNA can be obtained by subjecting the poly(A)mRNA fraction to acid-urea agarose gel electrophoresis or sucrose density gradient centrifugation.

To confirm that the resulting mRNA fraction is the desired one containing mRNA encoding rabbit TNF, the mRNA is made to translate into a protein and its biological activity is examined. This can be carried out, for example, by injecting the mRNA into the oocytes of *Xenopus laevis* or adding it to a suitable protein synthesizing system, such as a reticulocyte lysate or wheat germ cellfree system and by confirming that the translated protein has cytotoxic activity on mouse L-929 cells and this cytotoxic activity is neutralized by an antibody (the method of preparation is shown in Referential Example 3) against a purified rabbit plasma TNF (the method of production is shown in Referential Example 1).

I-2. Cloning of rabbit TNF cDNA

The mRNA fraction obtained in step I-1 above is used as a template, and an oligo(dT) or a pool of synthetic oligodeoxyribonucleotides having base sequences corresponding to a part of amino acid sequence of rabbit plasma TNF (see Referential Example 2 below) is used as a primer. A sscDNA complementary to the mRNA is synthesized by using reverse transcriptase [for example, that derived from avian myeloblastosis virus (AMV)] in the presence of dATP, dGTP, dCTP and dTTP. By alkali treatment, the template mRNA is hydrolyzed and removed. Then, the sscDNA is used as a template, and a dscDNA is synthesized by using reverse tanscriptase or *E. coli* DNA polymerase I (large fragment).

The resulting dscDNA is inserted, for example, into the restriction endonuclease Pst I cleavage site of plasmid pBR322 by a conventional method, for example the poly(dG)-poly(dC) homopolymer extension method [T. S. Nelson "Methods in Enzymology", 68, 41 (1979), Academic Press Inc., New York]. The resulting recombinant plasmid is introduced into a host such as *E. coli* 1776 in accordance with the method of Cohen et al. [Proc. Nat. Acad. Sci., USA, 60, 2110 (1972)] to transform it, and by selecting tetracycline-resistant colonies, a cDNA library is prepared.

The cDNA library is subjected to a colony hybridization assay [D. Hanahan et al., Gene, 10, 63 (1980)] by the plus-minus method, and the desired clones harboring recombinant plasmids containing a cDNA insert encoding rabbit TNF are screened by the following method.

$^{32}$P-labelled cDNA is sythesized using the enriched mRNA fraction with the rabbit TNF mRNA obtained in step I-1 as a template and used as an induction plus probe. Separately, a mRNA fraction, obtained by the same procedure as above except that non-induced alveolar macrophages from normal rabbits are used as a starting material, is used as a template and $^{32}$P-labelled cDNA is synthesized. The $^{32}$P-labelled cDNA is used as an induction minus probe. From the above cDNA library, plasmid clones which are strongly hybridized with the induction plus probe but not hybridized with the induction minus probe are selected.

The following method is carried out in order to confirm that the resulting clones harbor a cDNA insert encoding rabbit TNF. The plasmid DNAs are isolated from the above clones, converted to a single-stranded DNA by heating or alkali treatment, and fixed to a nitrocellulose filter. The mRNA fraction containing rabbit TNF mRNA is added to the filter to hybridize it. Then, the hybridized mRNA is eluted and recovered. The recovered mRNA is injected into the oocytes of *Xenopus laevis* to determine whether the recovered mRNA encodes rabbit TNF (to be referred to hereinbelow as the hybridization translation assay).

The above method gives clones of transformants containing the cloned plasmids having inserted thereinto a DNA fragment containing a base sequence complementary to the rabbit TNF mRNA.

When the cloned cDNAs do not contain the whole coding region of the rabbit TNF, cDNAs of a larger size are selected by screening the cDNA library using a cloned TNF cDNA fragment of the transformants cleaved with a suitable restriction endonuclease and labelled with $^{32}$P as a probe.

A cloned cDNA having a base sequence encoding a polypeptide containing the amino acid sequences of rabbit TNF can be obtained finally by analyzing the base sequences of some of the resulting cloned cDNA fragments in accordance with, for example, the Maxam-Gilbert method [Proc. Nat. Acad. Sci., USA, 74, 560 (1977)], thus searching for base sequences which encode the partial amino acid sequence (containing N- and C-terminals) of the rabbit plasma TNF (see Referential Example 2 below), and selecting cDNAs containing a base sequence corresponding to the whole coding region of TNF (the base sequence represented by formula [I] above).

The cloned cDNAs, by the determination of their base sequences to be described hereinbelow, have been found to include DNA having the base sequence of formula [II] and DNA having a base sequence corresponding to formula [II] in which AGT, the 87th codon from the 5'-terminal, is substituted by GGT.

Our investigations have shown that the cDNA encoding the polypeptide of rabbit TNF has the base sequence of formula [I] above or a base sequence corresponding to formula [I] in which AGT, the 7th codon from the 5'-terminal, is substituted by GGT.

The resulting cloned DNAs may be used as such, but as required, they may be modified to DNAs having or containing a base sequence corresponding to formula [I] or [II] in which (A) one or more codons are deleted, and/or (B) one or more codons are substituted by one or more other codons.

In the above cloned cDNA or the modified cDNAs thereof, one or more codons may be substituted by a degenerated codon or codons.

[II] Production of rabbit TNF polypeptide

A detailed description will follow of the process for producing the polypeptide of this invention having or containing rabbit TNF or a principal portion thereof by using the cloned DNA of this invention.

An expression vector for production of rabbit TN can be obtained by inserting the cloned DNA of the invention into a suitable vector. All vectors which proliferate in microorganisms to be transformed can be used. Examples include plasmids (*E. coli* plasmid pBR322), phages (such as λ phage derivatives), and viruses (such as SV40). They may be used singly or in combination, for example as a pBR322-SV40 hybrid plasmid. The site of insertion of DNA can be properly selected. In other words, a suitable site of a suitable vector may be cleaved by the action of a suitable restriction endonuclease in a customary manner, and the cloned cDNA of a suitable length may be inserted into the cleavage site.

More specifically, an expression vector for production of the non-fused polypeptide is constructed by joining a DNA fragment containing the base sequence of formula [I] encoding the amino acid sequence of formula [A], in which the initiation codon ATG is added to the 5'-terminal and the termination codon (TAA, TAG or TGA) exists at the 3'-terminal, to a DNA fragment with a suitable promoter and the Shine-Dalgarno sequence and inserting it into a vector. An expression vector for the production of the fused polypeptide may be constructed by inserting the cDNA fragment having the base sequence of formula [I] into the vector so that the translational reading frame coincides with that of the structure genes to be fused.

Examples of the promoters are lac, trp, tac, phoS, phoA, PL and SV40 early promoter.

Transformants are obtained by introducing the expression vector into a host such as microorganism, animal or plant cells. For example, *E. coli* are transformed by the method of Cohen et al. [Proc. Nat. Acad. Sci., USA, 69, 2110 (1972)]. Then, by cultivating one of the transformants, a polypeptide [A] or a polypeptide [A] with methionine at its N-terminal (to be sometimes abbreviated simply as the polypeptide [A]) is produced. The product can be accumulated either in the cytoplasm or in the periplasm of the host cells depending upon the method of constructing the expression vector. To cause the polypeptide to be secreted in the periplasm, one can construct an expression vector by using a gene coding for a secretory protein, such as alkaline phosphatase gene (phoA) or a phosphate binding protein gene (phoS), and joining DNA encoding the polypeptide [A] to the above gene at a suitable site following a DNA region encoding the signal peptide.

The resulting transformants are cultivated under suitable conditions for the transformants until the polypeptide [A] desired is fully produced. Then, the polypeptide [A] is extracted from the culture. When the produced polypeptide A is accumulated in the cytoplasm, the host cells are destroyed by lysozyme digestion and freezing and thawing or sonication or by using a French press, and then centrifuged or filtered to collect the extract. When it is accumulated in the periplasm, it can be extracted, for example, by the method of Willsky et al. [J. Bacteriol., 127, 595 (1976)].

The crude polypeptide [A] so obtained can be purified by general purifying methods for proteins, for example by combinations of ultrafiltration, dialysis, ion exchange chromatography, gel filtration, electrophoresis, affinity chromatography, etc.

Polypeptides in accordance with this invention other than the polypeptide [A] and a polypeptide with methionine at the N-terminal of the polypeptide [A] can be produced substantially in accordance with the above process, or by using proper combinations of known processes.

For formulating the polypeptides of this invention, they may be in the form of a solution or a lyophilized product. From the standpoint of long-term stability, they are desirably in the form of lyophilized products. It is preferred to add vehicles or stabilizers to the preparations. Examples of the stabilizers include albumin, globulin, gelatin, protamine, protamine salts, glucose, galactose, xylose, mannitol, glucuronic acid, trehalose, dextran, hydroxyethyl starch, and nonionic surface-active agents (such as polyoxyethylene fatty acid esters, polyoxyethylene alkyl ethers, polyoxyethylene alkyl phenyl ethers, polyoxyethylene sorbitan fatty acid esters, polyoxyethylene glycerin fatty acid esters, polyoxyethylene hardened castor oil, polyoxyethyene castor oil, polyoxyethylene polyoxypropylene alkyl ethers, polyoxyethylene polyoxypropylene block copolymer, sorbitan fatty acid esters, sucrose fatty acid esters and glycerin fatty acid esters).

The polypeptides of this invention are useful as antitumor agents because they have a selective cytotoxic effect on tumor cells and heal tumors of tumor-bearing animals.

Such polypeptide preparations are preferably administered parenterally or topically. Parenteral routes such as intravenous and intramuscular routes are used when tumor cells extend over a wide range or metastasize, or when prevention of metastasis is intended. Against local tumor tissues, direct intratumor administration is preferred. The dosage varies depending upon the type and size of tumors, the condition of the patient and the route of administration. Usually, it is $5 \times 10^2$ to $5 \times 10^7$ units/kg, preferably $5 \times 10^3$ to $5 \times 10^6$ units/kg (see Referential Example 2 given hereinafter in respect of units).

For simplification of the description, the following abbreviations are used in the present specification and claims.

| | |
|---|---|
| A: | adenine |
| C: | cytosine |
| G: | guanine |

-continued

| T: | thymine |
|---|---|
| Ala: | alanine |
| Arg: | arginine |
| Asn: | asparagine |
| Asp: | aspartic acid |
| Cys: | cysteine |
| Gln: | glutamine |
| Glu: | glutamic acid |
| Gly: | glycine |
| His: | histidine |
| Ile: | isoleucine |
| Leu: | leucine |
| Lys: | lysine |
| Met: | methionine |
| Phe: | phenylalanine |
| Pro: | proline |
| Ser: | serine |
| Thr: | threonine |
| Trp: | tryptophan |
| Tyr: | tyrosine |
| Val: | valine |
| DNA: | deoxyribonucleic acid |
| cDNA: | complementary DNA |
| RNA: | ribonucleic acid |
| mRNA: | messenger RNA |
| poly(A)mRNA: | poly(A)-containing mRNA |
| dATP: | deoxyadenosine triphosphate |
| dCTP: | deoxycytidine triphosphate |
| dGTP: | deoxyguanosine triphosphate |
| dTTP: | deoxythymidine triphosphate |
| oligo(dC): | oligodeoxycytidylic acid |
| oligo(dG): | oligodeoxyguanylic acid |
| oligo(dT): | oligodeoxythymidylic acid |
| poly(A): | polyadenylic acid |
| poly(U): | polyuridylic acid |
| poly(dA): | polydeoxyadenylic acid |
| poly(dC): | polydeoxycytidylic acid |
| poly(dG): | polydeoxyguanylic acid |
| poly(dT): | polydeoxythymidylic acid |
| ATP: | adenosine triphosphate |
| EDTA: | ethylenediaminetetraacetic acid |
| kb: | kilobase |
| kbp: | kilobase pair |
| bp: | base pair |

The following Examples and Referential Examples illustrate the present invention more specifically. It should be understood however that the invention is in no way limited to these examples.

For a better understanding of the following examples, FIGS. 1 to 4 are attached to the present specification.

EXAMPLE 1

Figure 1:
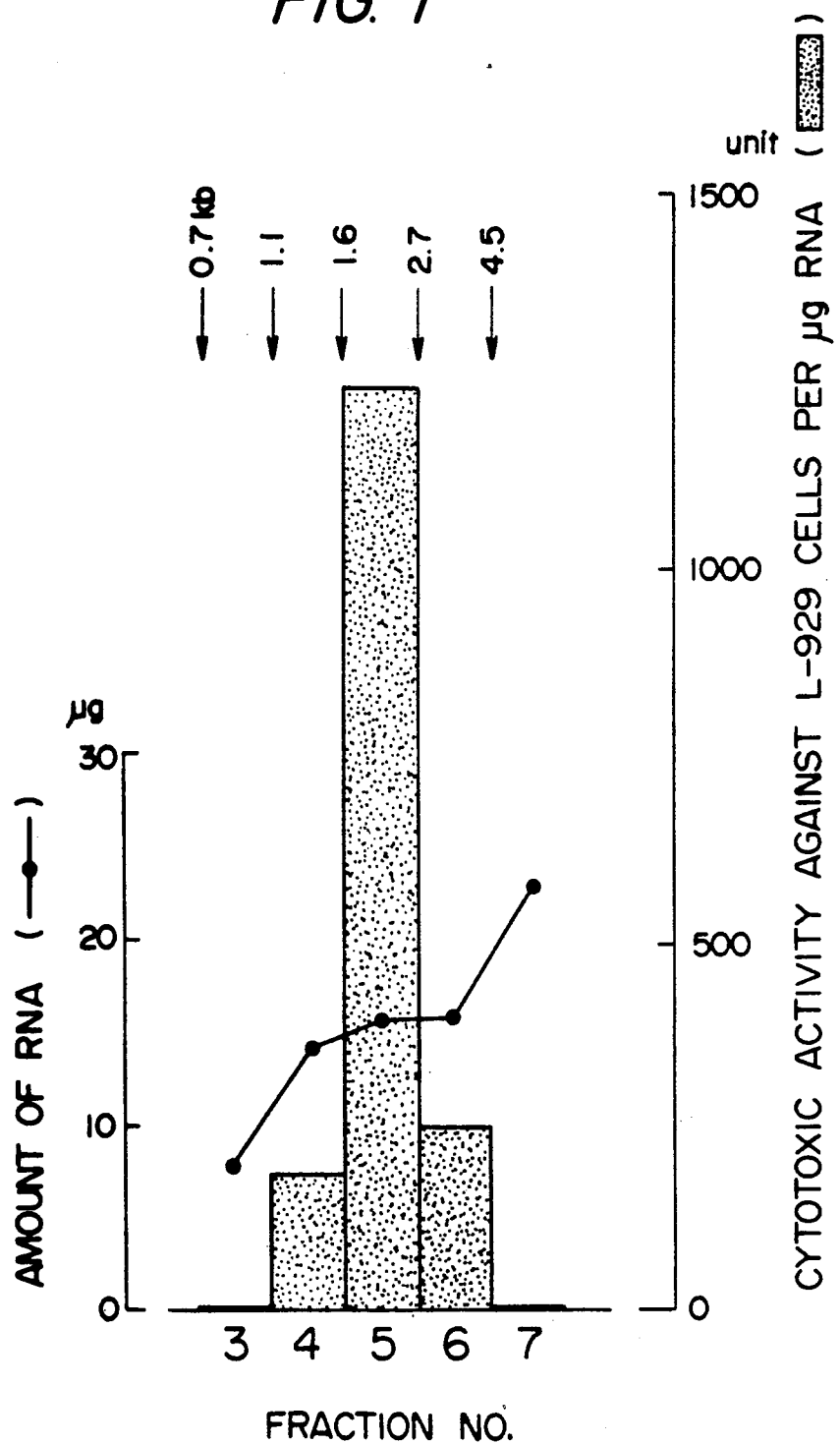
FIG. 1 is fractionation pattern of a rabbit TNF mRNA by acid-urea agarose gel electrophoresis [Example 1, (1)]

(1) Preparation of TNF mRNA from macrophages of rabbit alveolus

Rabbits (each having a body weight of about 2.5 kg) were intravenously injected with killed dried cells of *Propionibacterium acnes* at a dose of 100 mg per rabbit, and sacrificed 8 days later. The lungs were repeatedly washed with phosphate buffered saline through a tube inserted into the trachea of the animals, and alveolar macrophages were collected. About $3 \times 10^9$ alveolar macrophages were obtained from 12 rabbits.

The alveolar macrophages were suspended in RPMI-1640 medium containing 10% fetal bovine serum, and seeded in Petri dishes (8 cm in diameter) at a cell density of $2 \times 10^7$ cells per dish. They were pre-cultivated in air containing 5% carbon dioxide at 37° C. and a humidity of 90 to 100%. After pre-cultivation for one hour, an endotoxin (lipopolysaccharide derived from *E. coli*), TPA (phorbol-12-myristate-13-acetate) and cycloheximide (protein synthesis inhibitor) were added so that their final concentrations became 10 micrograms/ml, 10 ng/ml and 1 microgram/ml, respectively. The cultivation was further continued for 4 to 4.5 hours (total of 5 to 5.5 hours), the culture medium was removed by suction, and the macrophages adherent to the dishes were lysed and homogenized in a 5M guanidyl thiocyanate solution containing 0.6% sodium N-lauroyl sarcosinate and 6 mM sodium citrate. The homogenate was applied to a 5.7M cesium chloride solution containing 0.1M EDTA, and centrifuged for 20 hours at 26,500 rpm using an ultracentrifuge (RPS27-2 rotor, Hitachi Koki K.K.) to obtain a total RNA fraction as a pellet. The pellet was dissolved in a small amount of 7M urea solution containing 0.35M NaCl, 20 mM Tris and 20 mM EDTA and recovered by precipitation from ethanol. From 12 rabbits, 5.2 mg of total RNA were obtained.

The total RNA fraction was dissolved in 2 ml of 10 mM Tris-HCl (pH 7.4) buffer containing 1 mM EDTA (to be referred to as a TE solution), and the solution was heated at 65° C. for 5 minutes. A NaCl solution was added to a concentration of 0.5M, and the solution was applied onto a column of oligo(dT) cellulose previously equilibrated with the TE solution containing 0.5M NaCl. The column was eluted with the TE solution to give 314 micrograms of poly(A)mRNA. Two hundred micrograms of the resulting poly(A)mRNA was subjected to agarose gel electrophoresis (gel concentration 1%, in the presence of 6M urea, pH 4), and fractionated into 7 fractions according to molecular sizes. Poly(A)mRNA was isolated from each gel fractionated by melting at 70° C. for 10 minutes by successive extraction with phenol and chloroform and by precipitation from ethanol. The content of rabbit TNF mRNA in poly-(A)mRNA from each fraction was determined by a mRNA translation assay using oocytes of *Xenopus laevis*.

Each mRNA fraction was injected into the oocytes at a dose of about 50 ng per oocyte by a microinjection method. Ten oocytes were incubated in 100 microliters of the Barth medium [J. B.Gurdon, J. Embryol. Exp. Morphol., 20, 401 (1968)] at 22° C. for 24 hours. The oocytes were homogenized, and centrifuged (10,000 rpm, 10 minutes). The supernatant was subjected to assay of TNF activity by determining the cytotoxic activity against mouse L-929 cells.

Rabbit TNF mRNA was found at a high concentration in a fraction corresponding to a molecular size of 1.6 to 2.7 kb. This mRNA fraction had about 1,230 units of TNF activity per microgram of RNA, and was thus concentrated to about 4 fold from the starting poly-(A)mRNA preparation which had about 320 units of TNF activity per microgram of RNA (FIG. 1).

By using the purified anti-rabbit plasma TNF antibody prepared in Referential Example 3 given below, a test was conducted in order to confirm that protein translated in the oocytes injected with the resulting enriched mRNA fraction with rabbit TNF mRNA (to be abbreviated as enriched TNF mRNA) as a template had the same activity as that of rabbit plasma TNF. The supernatant of the oocyte homogenate, which was prepared from the oocytes injected with the enriched TNF mRNA fraction according to the method shown above, was used as an assay sample. Twenty microliters of the purified anti-rabbit plasma TNF antibody was added to 100 microliters of the assay sample and incubated at 37° C. for 2 hours. The cytotoxic activity of the reaction mixture against L-929 cells was determined. It was found that the cytotoxic activity was completely neutralized with the antibody. It shows that the protein translated in the oocytes is immunologically identical with the rabbit plasma TNF.

The enriched TNF mRNA fraction obtained herein was used in the following experiment.

(2) Synthesis of cDNA cDNA was synthesized under the following conditions. Four micrograms of the enriched TNF mRNA fraction was dissolved in 100 microliters of 50 mM Tris-HCl (pH 8.3) buffer containing 10 mM $MgCl_2$, 70 mM KCl, 1 mM dithiothreitol, 0.5 mM of each of the four deoxyribonucleotide triphosphates, dTTP, dCTP, dATP and dGTP (dCTP was labelled with $^{32}P$, specific activity $4.4 \times 10^6$ cpm/nmole), 3 micrograms of oligo$(dT)_{12-18}$ and 80 units of reverse transcriptase derived from avian myeloblastosis virus (AMV) and incubated at 43° C. for 90 minutes. Then the reaction was stopped by adding EDTA. The resulting cDNA-mRNA hybrid was extracted with phenol/chloroform (1:1), and recovered from the aqueous phase by precipitation from ethanol. The mRNA template was removed by treating with an alkali at 65° to 70° C. The synthesized sscDNA was recovered by precipitation from ethanol.

The sscDNA precipitate was dissolved in 40 microliters of a 0.1M Hepes (pH 6.9) buffer containing 0.5 mM of each of the four deoxyribonucleotide triphosphates, dATP, dTTP, dGTP and dCTP, 5 mM $MgCl_2$, 70 mM KCl, 1.5 mM 2-mercaptoethanol, and 8 units of *E. coli* DNA polymerase I (large fragment), and incubated at 15° C. for 20 hours to synthesize a dscDNA. The reaction was stopped by adding sodium dodecylsulfate. The dscDNA was extracted with phenol/chloroform, and recovered by precipitation from ethanol.

The resulting dscDNA was dissolved in 100 microliters of 50 mM sodium acetate (pH 4.5) containing 1 mM $ZnSO_4$, 200 mM NaCl, 0.5% glycerol and 0.5 unit of S1 nuclease and incubated at 37° C. for 20 minutes to cleave the hairpin structure. The reaction was stopped by adding EDTA. The reaction mixture was extracted with phenol/chloroform and then with diethyl ether. dscDNA was recovered by precipitation from ethanol.

(3) Preparation of oligo(dC)-tailed cDNA

The dscDNA obtained as above was dissolved in 100 microliters of 130 mM sodium cacodylate-30 mM Tris-HCl (pH 6.8) buffer containing 1 mM $CoCl_2$, 0.1 mM dithiothreitol, 0.2 microgram of poly(A), 0.1 mM $^3$H-dCTP (specific activity 5400 cpm/pmole) and 10 units of terminal deoxynucleotidyl transferase and incubated at 37° C. for 20 minutes to permit the addition of an oligo(dC) tail to the 3'-terminal of dscDNA.

The reaction was stopped by adding EDTA. The reaction mixture was extracted with phenol/chloroform and then with diethyl ether, and the oligo(dC)-tailed dscDNA was recovered by precipitation from ethanol. The oligo-(dC)-tailed dscDNA was dissolved in 10 mM Tris-HCl (pH 7.4) buffer containing 1mM EDTA and 100 mM NaCl so that it contained 0.2 microgram of the oligo(dC)-tailed dscDNA per ml.

(4) Preparation of oligo(dG)-tailed plasmid pBR322 DNA pBR322 (10 micrograms) was dissolved in 100 microliters of 20 mM Tris-HCl (pH 7.4) buffer containing 10 mM $MgCl_2$, 50 mM $(NH_4)_2SO_4$ and 10 micrograms of bovine serum albumine, and 15 units of restriction endonuclease PstI was added. The mixture was incubated at 37° C. for 1 hour. After the reaction was terminated, the reaction mixture was extracted with phenol/chloroform, and the resulting DNA was recovered from the aqueous phase by precipitation from ethanol. The DNA obtained was dissolved in 200 microliters of the same reaction buffer as used in tailing of the dscDNA above (except that it contained 80 units of terminal deoxynucleotidyl transferase and $^3$H-dGTP instead of $^3$H-dCTP) and incubated at 37° C. for 20 minutes to add about 10–15 dG residues per end. The reaction mixture was extracted with phenol/chloroform, and the oligo(dG)-tailed plasmid pBR322 DNA was recovered from the aqueous phase by ethanol precipitation. The resulting tailed plasmid DNA was dissolved in the same buffer as used in dissolving the oligo(dC)-tailed dscDNA so that it contained the tailed plasmid DNA in a concentration of 2 micrograms per ml.

(5) Construction of a recombinant plasmid

Fifty microliters of the oligo(dC)-tailed cDNA solution was mixed with 50 microliters of the oligo(dG)-tailed pBR322 DNA solution, and the mixture was incubated sequentially at 65° C. for 10 minutes, at 57° C. for 120 minutes, at 45° C. for 60 minutes, at 35° C. for 60 minutes and at room temperature for 60 minutes to perform annealing and thus construct a recombinant plasmid solution.

(6) Selection of transformants

*E. coli* 1776 strain was transformed with the recombinant plasmids obtained as above.

Specifically, *E. coli* X1776 was cultivated at 37° C. in 20 ml of L-broth (composition: 10 g of trypton, 5 g of yeast extract, 5 g of NaCl and 1 g of glucose per liter; pH 7.2) supplemented with 100 micrograms/ml of diaminopimelic acid and 40 micrograms/ml of thymidine until the turbidity at 600 nm reached 0.5. The cells were collected by centrifugation at 0° C., and washed with 10 mM Tris-HCl (pH 7.3) buffer containing 50 mM $CaCl_2$. The cells were resuspended in 2 ml of the same buffer as used above, and left to stand at 0° C. for 5 minutes. To 0.2 ml of the suspension was added 0.1 ml of the recombinant plasmid solution obtained as above. The mixture was left to stand at 0° C. for 15 minutes and then maintained at 42° C. for 2 minutes. Then, 0.5 ml of the supplemented L-broth as used above was added, and cultivation was carried out with shaking for 1 hour. An aliquot of the culture was taken, spread on the supplemented L-broth agar plate containing 15 micrograms/ml of tetracycline, and cultivated at 37° C. for about 12 hours. Transformants resistant to tetracycline were selected, and a cDNA library was prepared.

(7) Hybridization assay

Colony hybridization assay was conducted using a $^{32}$P-labelled cDNA probe by the method of Hanahan et al. [Gene, 10, 63 (1980)] in order to screen the cDNA library for transformants which had a plasmid containing cDNA encoding rabbit TNF. Induction plus and induction minus 32P-labelled ssCDNA probes were synthesized respectively by the method described in section (2) above using mRNAs obtained from induction plus and minus alveolar macrophages by the method described in section (1) as a template except that 32P-dCTP with high specific radioactivity was used. By this test, there were selected colonies of transformants harboring the recombinant plasmids which strongly hybridized with the induction plus probe but did not hybridize with the induction minus probe. Fifty colonies were selected from about 20,000 colonies.

Twenty out of the selected colonies were then subjected to mRNA hybridization translation assay by the method described in T. Maniatis et al. (ed) "Molecular Cloning", 329 (1980), Cold Spring Harbor Lab. The plasmid DNA was extracted from each of the transformants and fixed to a nitrocellulose filter after heat denaturation. The poly(A)mRNA fraction containing rabbit TNF mRNA obtained in section (1) above was added to the filter and incubated at 50° C. for 3 hours to perform hybridization. The hybridized mRNA was recovered and injected into the oocytes to determine whether the recovered mRNA was rabbit TNF mRNA. As a result of this test, three colonies were found which had plasmids containing cDNAs that strongly hybridized with the rabbit TNF mRNA. cDNA fragments were obtained from the plasmid having cDNA of the largest size (about 750 bp) by digestion with restriction endonuclease DdeI, and used as a probe for further screening. These DNA fragments were labelled with 32P. By using these probes, the cDNA library obtained in section (6) above was screened by colony hybridization assay, and colonies of transformants having plasmids containing cDNAs which strongly hybridized with the labelled probes were selected. 98 out of about 60,000 colonies of the cDNA library were found to be positive in this test. The recombinant plasmid DNA was isolated and cDNA inserts were cut out from these recombinant plasmids by digestion with restriction endonuclease PstI, and their sizes were measured by polyacrylamide gel electrophoresis. Seventeen clones of transformants having cDNA inserts of at least 1 kbp were selected. From a transformant containing cDNA of the largest size (transformant No: X1776/pRTNF802; plasmid No.: pRTNF802), the cloned cDNA was isolated, and its base sequence was determined by the following method.

(8) Determination of the base sequence of the cloned cDNA

The transformant (X1776/pRTNF802) selected in section (7) above was cultivated in L-broth supplemented with diaminopimelic acid and thymidine. The cells were treated in accordance with the method of Wilkie et al. [Nucleic Acids Res., 7, 859 (1979)] to obtain a plasmid DNA. The plasmid DNA was cleaved with restriction endonuclease PstI, and purified to obtain a cloned cDNA. The cloned cDNA fragment was cleaved with various restriction endonucleases, and the base sequences of suitable restriction endonuclease-cleaved fragments were determined by the method of Maxam-Gilbert.

Figure 2:
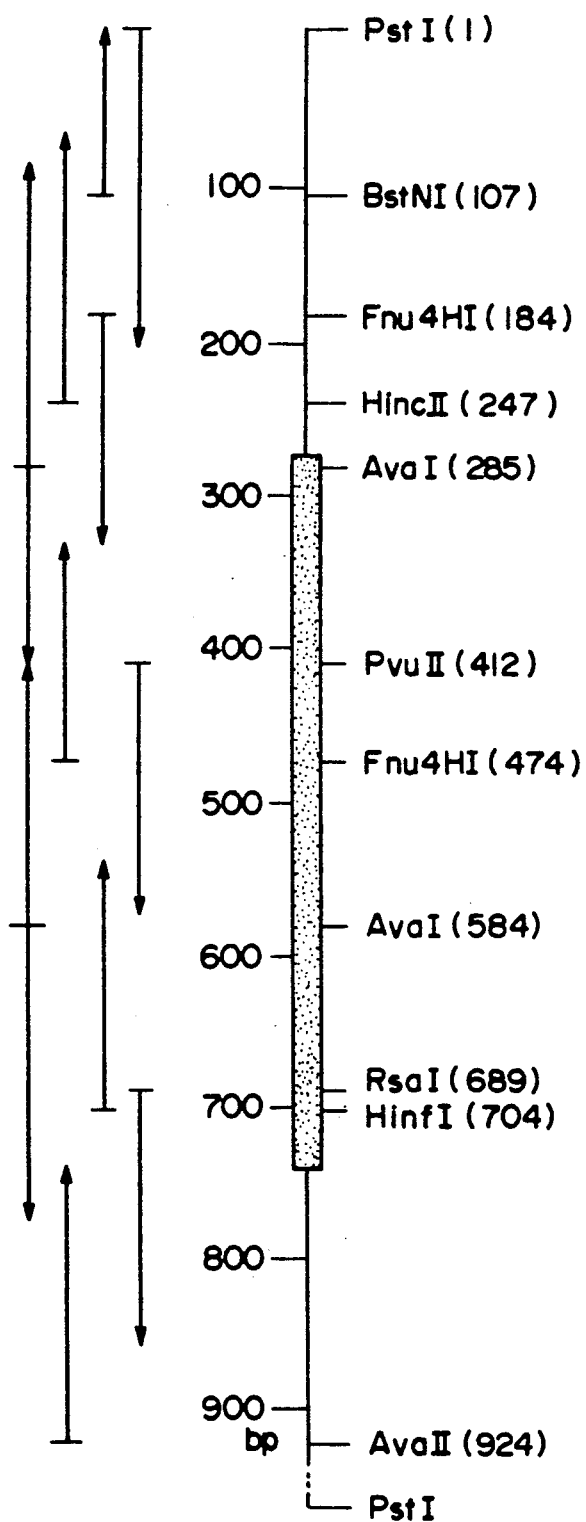
FIG. 2 shows the restriction endonuclease cleavage sites and sizes of DNA fragments used in determining the base sequence of cloned cDNA (plasmid pRTNF802) encoding rabbit TNF [Example 1, (8)]

FIG. 2 shows the restriction endonuclease cleavage sites used in determining the base sequences and the directions and extents of sequence determination indicated by arrows. The dotted rectangular area is a coding region for rabbit TNF.

The base sequence determined is shown in Table 1 below. In Table 1, the first 15 bases are an oligo(dG) tail added for insertion of cDNA into the vector. The 34th to 276th bases are a base sequence which is presumed to encode a polypeptide required for constituting a precursor of rabbit TNF. The 277th to 291st bases encode an amino acid sequence corresponding to the N-terminal portion elucidated in Referential Example 2 with regard to the rabbit plasma TNF (the segment surrounded by a rectangle in Table 1). The 715th to 738th bases encode the amino acid sequence of the C-terminal portion. There is the termination codon (TGA) following the codon of the C-terminal amino acid (leucine).

TABLE 1

```
              10            20            30
               |             |             |
      GGGGGGGGGGGGGGGGCCCTCTGGAGAGAGC
              40            50            60
               |             |             |
      GCCATGAGCACTGAGAGTATGATCCGGGAC
          Met Ser Thr Glu Ser Met Ile Arg Asp
              70            80            90
               |             |             |
      GTCGAGCTGGCGGAGGGGCCGCTCCCCAAG
          Val Glu Leu Ala Glu Gly Pro Leu Pro Lys
             100           110           120
               |             |             |
      AAGGCAGGGGGGCCCCAGGGCTCCAAGCGC
          Lys Ala Gly Gly Pro Gln Gly Ser Lys Arg
             130           140           150
               |             |             |
      TGCCTCTGCCTCAGCCTCTTCTCTTTCCTG
          Cys Leu Cys Leu Ser Leu Phe Ser Phe Leu
             160           170           180
               |             |             |
      CTCGTGGCTGGAGCCACCACGCTCTTCTGC
          Leu Val Ala Gly Ala Thr Thr Leu Phe Cys
             190           200           210
               |             |             |
      CTGCTGCACTTCAGGGTGATCGGCCCTCAG
          Leu Leu His Phe Arg Val Ile Gly Pro Gln
             220           230           240
               |             |             |
      GAGGAAGAGCAGTCCCCAAACAACCTCCAT
          Glu Glu Glu Gln Ser Pro Asn Asn Leu His
             250           260           270
               |             |             |
      CTAGTCAACCCTGTGGCCCAGATGGTCACC
          Leu Val Asn Pro Val Ala Gln Met Val Thr
             280           290           300
               |             |             |
      CTCAGATCAGCTTCTCGGGCCCTGAGTGAC
          Leu Arg |Ser Ala Ser Arg Ala| Leu Ser Asp
             310           320           330
               |             |             |
      AAGCCTCTAGCCCACGTAGTAGCAAACCCG
          Lys Pro Leu Ala His Val Val Ala Asn Pro
             340           350           360
               |             |             |
      CAAGTGGAGGGCCAGCTCCAGTGGCTGAGC
          Gln Val Glu Gly Gln Leu Gln Trp Leu Ser
             370           380           390
               |             |             |
      CAGCGTGCGAACGCCCTGCTGGCCAACGGC
          Gln Arg Ala Asn Ala Leu Leu Ala Asn Gly
             400           410           420
               |             |             |
      ATGAAGCTCACGGACAACCAGCTGGTGGTG
          Met Lys Leu Thr Asp Asn Gln Leu Val Val
             430           440           450
               |             |             |
      CCGGCCGACGGGCTGTACCTCATCTACTCC
          Pro Ala Asp Gly Leu Tyr Leu Ile Tyr Ser
             460           470           480
               |             |             |
      CAGGTTCTCTTCAGCGGTCAAGGCTGCCGC
          Gln Val Leu Phe Ser Gly Gln Gly Cys Arg
             490           500           510
               |             |             |
      TCCTACGTGCTCCTCACTCACACTGTCAGC
          Ser Tyr Val Leu Leu Thr His Thr Val Ser
```

TABLE 1-continued

```
            520           530           540
             |             |             |
        CGCTTCGCCGTCTCCTACCCGAACAAGGTC
        Arg Phe Ala Val Ser Tyr Pro Asn Lys Val
            550           560           570
             |             |             |
        AACCTCCTCTCTGCCATCAAGAGCCCCTGC
        Asn Leu Leu Ser Ala Ile Lys Ser Pro Cys
            580           590           600
             |             |             |
        CACCGGGAGACCCCCGAGGAGGCTGAGCCC
        His Arg Glu Thr Pro Glu Glu Ala Glu Pro
            610           620           630
             |             |             |
        ATGGCCTGGTACGAGCCCATCTACCTGGGC
        Met Ala Trp Tyr Glu Pro Ile Tyr Leu Gly
            640           650           660
             |             |             |
        GGCGTCTTCCAGTTGGAGAAGGGTGACCGG
        Gly Val Phe Gln Leu Glu Lys Gly Asp Arg
            670           680           690
             |             |             |
        CTCAGCACCGAGGTCAACCAGCCTGAGTAC
        Leu Ser Thr Glu Val Asn Gln Pro Glu Tyr
            700           710           720
             |             |             |
        CTGGACCTTGCCGAGTCCGGGCAGGTCTAC
        Leu Asp Leu Ala Glu Ser Gly Gln Val Tyr
            730           740           750
             |             |             |
        TTTGGGATCATTGCCCTGTGAGGGGACTGA
        Phe Gly Ile Ile Ala Leu
            760           770           780
             |             |             |
        CCACCACTCCTCCCCCTCTCCCACCCCAGC
            790           800
             |             |
        CCCCTCACTCTGGGCGCCCTCAG
```

The number of amino acid residues which are deduced from the base sequence (277th to 738th) encoding the rabbit TNF polypeptide is 154, and its amino acid composition and calculated molecular weight are shown in Table 2 below. The amino acid composition and molecular weight agreed within the range of experimental errors with the amino acid composition of the rabbit plasma TNF and its measured molecular weight shown in Referential Example 2.

TABLE 2

| Amino acid | Amino acid composition (mole) deduced from the base sequence |
|---|---|
| Asp | 5 |
| Asn | 7 |
| Thr | 5 |
| Ser | 13 |
| Glu | 10 |
| Gln | 10 |
| Pro | 9 |
| Gly | 10 |
| Ala | 14 |
| Cys | 2 |
| Val | 13 |
| Met | 2 |
| Ile | 5 |
| Leu | 21 |
| Tyr | 8 |
| Phe | 4 |
| His | 3 |
| Lys | 5 |
| Arg | 6 |
| Trp | 2 |
| Total number of residues | 154 |
| Calculated molecular weight | 16,997 daltons |

EXAMPLE 2

Production of rabbit TNF polypeptide

A DNA fragment having a size of 513 bp was cut out from the cloned cDNA (see Table 1) encoding rabbit TNF obtained in Example 1 by using restriction endonucleases AvaI and HaeII, and joined to the downstream of a tac promoter region with a synthetic oligodeoxyribonucleotide adaptor. The resulting TNF fragment was inserted into plasmid pBR322 DNA to construct an expression vector. The details of this procedure were as follows (see FIG. 3 also). The plasmid pRTNF802 DNA (350 micrograms) obtained in Example 1, (7) (having inserted thereinto cDNA encoding rabbit TNF) was digested with restriction endonucleases HaeII (600 units) and Tth111I (840 units) by incubation at 37° C. for 60 minutes, further at 65° C. for 60 minutes. The digested DNA fragments were recovered by precipitation from ethanol. They were dissolved in 0.6 ml of a TBE solution (50 mM Tris, 50 mM boric acid and 1 mM EDTA) and a 677 bp DNA fragment containing a region encoding rabbit TNF (to be referred to as RTNF-DNA fragment) and a 227 bp DNA fragment (to be referred to as the HaeII-HaeII fragment) were isolated by 5% polyacrylamide gel electrophoresis. The RTNF DNA fragment corresponds to the base sequence composed of the 121st to 797th bases shown in Table 1.

Twenty micrograms of the RTNF DNA fragment was incubated at 37° C. for 35 minutes in 0.4 ml of 10 mM Tris-HCl (pH 7.5) buffer containing 50 mM NaCl, 6 mM MgCl$_2$ and 6 mM 2-mercaptoethanol with 320 units of restriction endonuclease AvaI, and the digested DNA fragments were recovered by precipitation from ethanol. The digested DNA fragments were dissolved in 10 mM Tris-HCl (pH 8.0) buffer containing 1 mM EDTA, and a 513 bp DNA fragment corresponding to the 285th to 797th bases shown in Table 1 (to be referred to as RTNF'-DNA fragment) was isolated by 5% polyacrylamide gel electrophoresis.

The tac promoter region was cut out from tac promoter vector pDR540 [D. R. Russell et al., Gene, 20, 231 (1982); purchased from P-L Biochemicals (USA)] by using restriction endonucleases HindIII and BamHI, and a 92 bp DNA fragment containing the tac promoter region (to be referred to as the tac promoter fragment) was isolated by polyacrylamide gel electrophoresis.

The above tac promoter fragment and the RTNF'-DNA fragment were ligated through a chemically synthesized oligodeoxyribonucleotide adaptor. This synthetic adaptor is represented by the following formula, and its two ends are BamHI and AvaI cohesive termini.

The above procedure gave a DNA fragment containing the tac promoter followed by the initiation codon ATG and further by the entire rabbit TNF coding region (to be referred to as the tac promoter-RTNF-DNA fragment).

Six micrograms of the HaeII-HaeII fragment obtained as above was digested with restriction endonuclease SalI (1600 units) in 10 mM Tris-HCl (pH 7.5) buffer containing 200 mM NaCl, 6 mM MgCl$_2$, 6 mM 2-mercaptoethanol by incubation at 37° C. for 90 minutes. Subsequent ethanol precipitation and polyacrylamide gel electrophoresis as above led to the isolation of a 99 bp DNA fragment (to be referred to as the HaeII-SalI fragment).

Separately, from plasmid pBR322 (4362 bp) a 3741 bp DNA fragment containing an ampicillin-resistance gene (to be referred to as the HindIII-SalI fragment) was cut out by digesting with restriction endonucleases HindIII and SalI in a customary manner.

Figure 3:
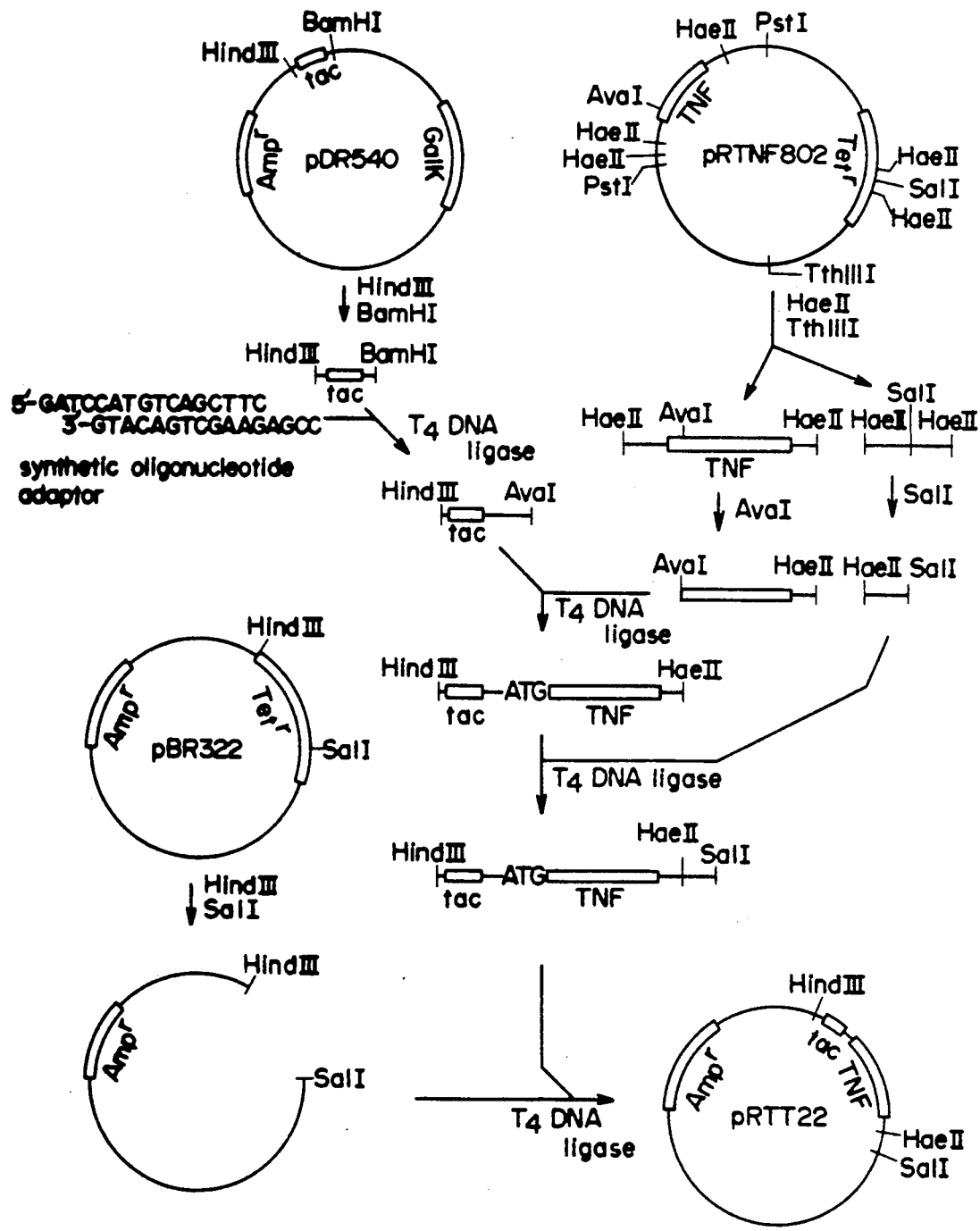
FIG. 3 shows a process of constructing an expression vector pRTT22 (Example 2)

The HindIII-SalI fragment was ligated with the previously prepared tac promoter-RTNF-DNA fragment and HaeII-SalI fragment by means of T4 DNA ligase to construct an expression vector (pRTT22) for production of rabbit TNF (see FIG. 3).

The resulting recombinant plasmid pRTT22 was introduced into E. coli JM103 [lacI$^Q$; D. R. Russell et al., Gene, 20, 231 (1982); purchased from P-L Biochemicals] by the following method.

E. coli JM103 was inoculated in 5 ml of LB broth (composition: 10 g of trypton, 5 g of yeast extract, 10 g of NaCl per liter; pH 7.5) and cultivated overnight at 37° C. One milliliter of the resulting culture was inoculated in 100 ml of LB broth, and further cultivated at 37° C. until the turbidity at 650 nm of the culture reached 0.6. After standing for 30 minutes in ice water, the cells were collected by centrifugation and suspended in 50 ml of 50 mM $CaCl_2$, followed by standing at 0° C. for 60 minutes. The cells were then collected by centrifugation and again suspended in 10 ml of 50 mM $Cacl_2$ containing 20% glycerol and used as the calcium-treated E. coli JM103.

The recombinant plasmid pRTT22 was mixed with the calcium-treated E. coli JM103 suspension. The mixture was incubated in ice water for 20 minutes, then at 42° C. for 1 minute and further at room temperature for 10 minutes, and the LB broth was added. The mixture was shaken at 37° C. for 60 minutes. An aliquot of the resulting cell suspension was seeded in LB agar plates containing 25 micrograms/ml of ampicillin, and cultivated overnight at 37° C. Then, ampicillin-resistant colonies were selected to obtain transformants. One of the transformants for production of rabbit TNF was named JM103/pRTT22.

The transformants (JM103/pRTT22) were cultivated overnight in the LB broth containing 25 micrograms/ml of ampicillin. The culture was inoculated in 10 times its volume of the modified M9 medium (composition: 0.7% $Na_2HPO_4.12H_2O$, 0.3% $KH$ 0.05% NaCl, 0.1% $NH_4Cl$, 2 mg/liter vitamin $B_1$, 0.45% casamino acid, 1 mM $MgSO_4$, 0.1 mM $CaCl_2$, 0.5% glucose, 25 micrograms/ml ampicillin), and cultivated at 37° C. for 1 hour. Then, isopropyl beta-D-thiogalactoside was added to a final concentration of 1 mM, and the cultivation was continued further for 4 hours. Then, the cells were collected by centrifugation. The cells were suspended in a 50 mM Tris-HCl (pH 8.0) buffer containing 0.1% lysozyme and 30 mM NaCl in one-tenth of the volume of the culture, and left to stand at 0° C. for 30 minutes. Further, freezing on a dry ice/ethanol bath and thawing at 37° C. were repeated, and the cell debris was removed by centrifugation to give a clarified lysate.

The TNF activity (L-929 cell cytotoxic activity) of the extract was $2.4 \times 10^3$ units/ml.

This cytotoxic activity was completely neutralized with an antibody to rabbit plasma TNF shown in Referential Example 3.

EXAMPLE 3

In the 98 positive colonies selected by second screening of the cDNA library by colony hybridization assay as shown in Example 1, (7), there were 17 clones harboring recombinant plasmids containing TNF cDNA inserts having a size of at least 1 kbp. The individual cDNA inserts were cut out from these 17 clones using restriction endonuclease PstI, and a restriction map was constructed for each cDNA insert by using various restriction endonucleases. It was found that 15 clones seemed to represent almost the same restriction map as pRTNF802 obtained in Example 1, but 2 clones had an additional restriction cleavage site for endonuclease AvaI in a non-coding region about 250 bp downstream of the coding region for rabbit TNF. This AvaI restriction cleavage site was not observed in the 15 clones mentioned above.

With regard to a plasmid having another type of cDNA inserted thereinto (named pRTNF865), the base sequence of the coding region for rabbit TNF was determined by the method of Maxam-Gilbert in the same way as shown in Example 1, (8). It was consequently found that from the 285th base to the 741st base, only one base, i.e. A in the 295th position, was substituted by G in the base sequence shown in Table 1. Accordingly, the above cDNA is considered to be an allelic mutant of the cDNA obtained in Example 1.

Figure 4:
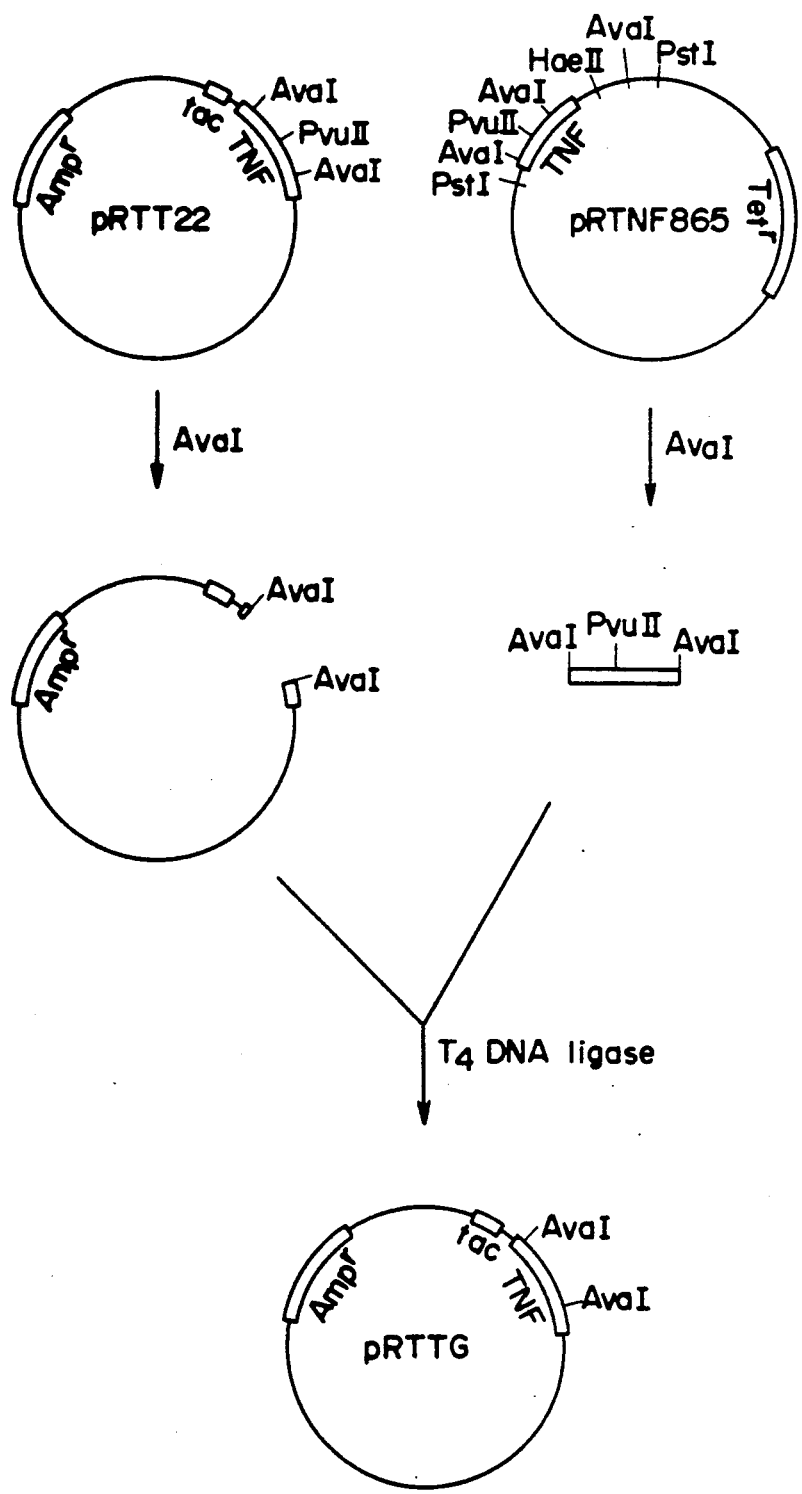
FIG. 4 shows a process for constructing an experession vector pRTTG (Example 3).

Then, a fragment of the cDNA inserted into plasmid pRTNF865, namely a DNA fragment corresponding to the 285th base to the 583rd base in Table 1 except that the 295th base is G, was cut out by using restriction endonuclease AvaI (to be referred to as the AvaI-AvaI fragment). The AvaI-AvaI fragment was inserted into a plasmid resulting from deletion of the same site of the region encoding rabbit TNF from the expression plasmid pRTT22 indicated in Example 2 by partial digestion with restriction endonuclease AvaI. This new expression vector in which the AvaI-AvaI fragment from pRTNF865 was inserted in the correct orientation was selected, and named pRTTG (see FIG. 4).

By the same method as shown in Example 2, this expression vector was introduced into E. coli JM103, the resulting transformant was cultivated, and the cell lysate was prepared by the same manner as shown in Example 2. The TNF activity of the lysate was $2.6 \times 10^3$ units/ml.

The foregoing experimental fact shows that a polypeptide was produced in which only one amino acid was different from the TNF polypeptide shown in Example 1, namely the seventh amino acid from the N-terminal (excluding Met derived from the initiation codon ATG) i.e. Ser, was replaced by Gly, and that this polypeptide had cytotoxic activity.

REFERENTIAL EXAMPLE 1

Isolation and purification of rabbit plasma TNF

Rabbits (body weight 2.5 to 3.0 kg) were injected intravenously with 50 mg of killed dried cells of Propionibacterium acnes from the, ear vein. Eight days later, the rabbits were injected with 100 micrograms of endotoxin (lipopolysaccharide derived from E. coli) from the ear vein. Two hours later, blood was taken from each rabbit by cardiac puncture. The blood was mixed with 100 units of sodium heparin per 100 ml, and then centrifuged at 5,000 rpm for 30 minutes under cooling to remove blood cells and insoluble matters. Twenty-four liters of the plasma was obtained from 400 rabbits.

EDTA (24 g) and 240 g of celite were added to 24 liters of the plasma, and the mixture was stirred for 1 hour and then filtered successively through filters having a pore size of 3 microns, 1 micron and 0.2 micron.

To 24 liters of the filtrate was added 12 liters of 0.04M Tris-HCl (pH 7.8) buffer, and the mixture was applied onto a column (27×45 cm) of DEAE-Sepharose CL-6B (Pharmacia) equilibrated with 0.04M Tris-HCl (pH 7.8) buffer containing 0.1M NaCl. The column was then washed with 75 liters of 0.04M Tris-HCl (pH 7.8) buffer containing 0.1M NaCl and then with 50 liters of 0.04M Tris-HCl (pH 7.8) buffer containing 0.15M NaCl, and then eluted with 0.04M Tris-HCl (pH 7.2) buffer containing 0.18M NaCl. The eluate was fractionated into 8-liter fractions, and active fractions having cytotoxic activity were collected. The active fractions were pooled and diluted with an equal volume of 0.04M Tris-HCl (pH 7.8) buffer. The diluted solution was applied onto a column (10×13 cm) of DEAE-Sepharose CL-6B. The column was washed with 1 liter of 0.04M Tris-HCl (pH 7.8) buffer containing 0.1M NaCl and then eluted with 5 liters of 0.04M Tris-HCl (pH 7.2) buffer containing 0.18M NaCl. The eluate was fractionated into 250 ml fractions and fractions having cytotoxic activity on L-929 cells were collected and pooled.

The active fraction was heated at 60° C. for 30 minutes and rapidly cooled to 4° C.. The cooled solution was concentrated by ultrafiltration.

The resulting concentrate was applied onto a column (5×80 cm) of Sephacryl S-200 (Pharmacia) equilibrated with 0.005M phosphate (pH 7.4) buffer containing 0.1 M NaCl, and eluted with the same buffer. The eluate was fractionated into 40 ml fractions, and active fractions were collected, pooled and concentrated by ultrafiltration.

The concentrate of the active fraction obtained by gel filtration was applied onto a column of $Zn^{2+}$ chelate Sepharose as shown below. A column (1.6×20 cm) filled with chelate Sepharose (iminodiacetic acid fixed resin) prepared by the method of J. Porath et al., [Nature, 258, 598 (1975)] was washed with 120 ml of a zinc chloride solution (1 mg/ml) and then equilibrated with 0.05M phosphate (pH 7.4) buffer containing 0.1M NaCl. Then, the concentrate obtained in the previous step was applied onto the column, and eluted with the same buffer. Fractions not adsorbed on the column were collected. Activity was almost completely recovered in these fractions.

The active fractions obtained in the previous step were concentrated and applied onto a column (1.5×90 cm) of Toyopearl HW-55 (a product of Toyo Soda Co., Ltd.) fully equilibrated with 0.005M phosphate (pH 7.4) buffer containing 0.15M NaCl. The column was eluted with the same buffer, and active fractions were pooled. This preparation was a purified rabbit plasma TNF.

REFERENTIAL EXAMPLE 1

Properties of the rabbit plasma TNF

The cytotoxic activity against mouse L-929 cells and the antitumor activity against Meth A sarcoma transplanted into mice were evaluated on the purified rabbit plasma TNF isolated in Referential Example 1.

The method of measuring the cytotoxic activity on L-929 cells was as follows:

A TNF sample (0.1 ml) diluted serially in a medium and 0.1 ml of a suspension of L-929 cells ($5 \times 10^5$/ml) containing actinomycin D (2 micrograms/ml) were added into each well using a 96 well microtiter plate (Flow Laboratories). The Eagle minimum essential medium containing 1% (v/v) of fetal bovine serum was used. The plate was incubated at 37° C. for 18 hours in air containing 5% of carbon dioxide. After the incubation, 20 microliters of glutaraldehyde was added to fix the viable cells. After fixation, the microplate was washed and dried. Then, 0.1 ml of 0.05% methylene blue solution was added to dye the fixed cells. The excess of methylene blue was washed off, and the plate was dried. Methylene blue associated with the fixed cells was eluted with 0.36N HCl and its absorbance at 665 nm was measured by a Titertek Multiscan (Flow Laboratories). The absorbance is proportional to the number of viable cells. The amount of biological activity required to kill 50% of the L-929 cells was defined as one unit/ml, and the dilution ratio of the sample corresponding to a 50% value of the absorbance of a control to which the sample was not added was determined from a graph or by calculation. The reciprocal of the dilution ratio is defined as the biological activity (units/ml) in the sample.

The cytotoxic activity against L-929 cells of 1 mg of the purified rabbit plasma TNF was about $3 \times 10^7$ units.

The antitumor effect on mice bearing Meth-A sarcoma was evaluated by the following method.

Into the abdominal skin of BALB/c mice were subcutaneously transplanted $2 \times 10^5$ Meth-A cells, and seven days later, mice were selected in which a tumor, 6–7 mm in diameter, was formed. Into the tumor mass $3 \times 10^4$ units of the purified rabbit plasma TNF was injected. Within 24 hours after the injection, a necrotic response was observed in the tumor transplant, and the tumor was completely cured within 14 days.

The molecular weight of the purified rabbit plasma TNF was measured by gel filtration analysis in accordance with high-performance liquid chromatography in the presence and absence of 8M urea. As a result, TNF derived from the rabbit plasma had a molecular weight of about 45,000 daltons in the absence of urea. In the presence of urea, it was dissociated into a single polypeptide which was found to have a molecular weight of about 16,000 daltons. The molecular weight in the presence of urea, namely in the completely dissociated state, is considered to be the molecular weight of the monomer of the rabbit TNF.

The amino acid composition of the rabbit plasma TNF was determined by a micro amino acid analyzer (made by Shimadzu Seisakusho) in accordance with a fluorometric method using orthophthalaldehyde after the sample was hydrolyzed with hydrochloric acid. The results are tabulated in Table 3.

TABLE 3

| Amino acid | Relative molar quantities |
| --- | --- |
| Asp + Asn | 12.2 (12) |
| Thr | 4.7 (5) |
| Ser | 12.0 (12) |
| Glu + Gln | 19.9 (20) |
| Pro | 10.1 (10) |
| Gly | 10.2 (10) |
| Ala | 14.2 (14) |
| Cys | 1.7 (2) |
| Val | 12.8 (13) |
| Met | 1.7 (2) |
| Ile | 5.0 (5) |
| Leu | 20.9 (21) |
| Tyr | 6.6 (7) |

TABLE 3-continued

| Amino acid | Relative molar quantities |
| --- | --- |
| Phe | 3.8 (4) |
| His | 2.8 (3) |
| Lys | 5.4 (5) |
| Arg | 6.1 (6) |
| Trp | Not measured |

The partial amino acid sequence including the N-terminal and C-terminal were analyzed by the Edman degradation method, the hydrazine degradation method, and the enzymatic method using carboxypeptidase. It was consequently found that the amino acid sequences at the N-terminal and C-terminal portions were as follows:

N-terminal: Ser—Ala—Ser—Arg—Ala ...
C-terminal: ... Val—Tyr—Phe—Gly—Ile—Ile—Ala—Leu

REFERENTIAL EXAMPLE 3

Preparation of an anti-rabbit plasma TNF antibody

TNF solution containing $1 \times 10^6$ units of the purified rabbit plasma TNF obtained in Referential Example 1 was emulsified with an equal volume of the Freund's complete adjuvant, and the emulsion was injected subcutaneously into the back of guinea pigs at several parts. Then, the animals were immunized by the same method 1, 3 and 6 weeks later. Furthermore, 8 weeks later, the same amount of the purified rabbit plasma TNF was intraperitoneally injected together with aluminum hydroxide gel. The whole blood was taken by cardiac puncture 9 weeks after the first immunization, and centrifuged to obtain an antiserum containing an anti-rabbit plasma TNF antibody.

The antiserum was passed through a column of Sepharose 4B coupled with serum protein components of normal rabbits. By repeating it 3 times a purified antibody specific for the rabbit plasma TNF was obtained. It was confirmed by immunoelectrophoresis and gel double diffusion methods that this antibody formed a single precipitation line only with the purified rabbit plasma TNF.

An about 60,000-fold dilution of this purified antibody has the ability of neutralizing 50% of 500 units of the cytotoxic activity of the rabbit plasma TNF against L-929 cells.

What we claim is:

1. A recombinant DNA consisting essentially of a base sequence encoding a rabbit tumor necrosis factor polypeptide.

2. A recombinant DNA consisting essentially of a base sequence corresponding to an amino acid sequence of the following formula:

Ser Ala Ser Arg Ala Leu Ser Asp Lys Pro    [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.

3. A recombinant DNA consisting essentially of a base sequence represented by the following formula:

(5')-TCA GCT TCT CGG GCC CTG AGT GAC AAG    [I]
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3').

4. A recombinant DNA consisting essentially of a base sequence corresponding to an amino acid sequence of the following formula:

Ser Thr Glu Ser Met Ile Arg Asp Val Glu    [B]
Leu Ala Glu Gly Pro Leu Pro Lys Lys Ala
Gly Gly Pro Gln Gly Ser Lys Arg Cys Leu
Cys Leu Ser Leu Phe Ser Phe Leu Leu Val
Ala Gly Ala Thr Thr Leu Phe Cys Leu Leu
His Phe Arg Val Ile Gly Pro Gln Glu Glu
Glu Gln Ser Pro Asn Asn Leu His Leu Val
Asn Pro Val Ala Gln Met Val Thr Leu Arg
Ser Ala Ser Arg Ala Leu Ser Asp Lys Pro
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.

5. A recombinant DNA consisting essentially of a base sequence represented by the following formula:

(5')-AGC ACT GAG AGT ATG ATC CGG GAC GTC    [II]
GAG CTG GCG GAG GGG CCG CTC CCC AAG AAG
GCA GGG GGG CCC CAG GGC TCC AAG CGC TGC
CTC TGC CTC AGC CTC TTC TCT TTC CTG CTC
GTG GCT GGA GCC ACC ACG CTC TTC TGC CTG
CTG CAC TTC AGG GTG ATC GGC CCT CAG GAG
GAA GAG CAG TCC CCA AAC AAC CTC CAT CTA
GTC AAC CCT GTG GCC CAG ATG GTC ACC CTC
AGA TCA GCT TCT CGG GCC CTG AGT GAC AAG
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC

-continued
AGC ACC GAG GTC AAC CAG CCT GAG TAC CTG
GAC CTT GCC GAG TCC GGG CAG GTC TAC TTT
GGG ATC ATT GCC CTG-(3').

6. A process for producing a polypeptide consisting of an amino acid sequence represented by the following formula:

Ser Ala Ser Arg Ala Leu Ser Asp Lys Pro          [A]
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg
    Glu Thr Pro Glu Glu Ala Glu Pro Met Ala
    Trp Tyr Glu Pro Ile Tyr Leu Gly Gly Val
    Phe Gln Leu Glu Lys Gly Asp Arg Leu Ser
    Thr Glu Val Asn Gln Pro Glu Tyr Leu Asp
    Leu Ala Glu Ser Gly Gln Val Tyr Phe Gly
    Ile Ile Ala Leu which comprises inserting a DNA of claim 2 into an expression vector, transforming a host with the vector, cultivating the host, and collecting the polypeptide.

7. A recombinant DNA consisting essentially of a base sequence corresponding to an amino acid sequence of formula Ser Ala Ser Arg Ala Leu Ser Asp Lys Pro          [A]
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg
    Glu Thr Pro Glu Glu Ala Glu Pro Met Ala
    Trp Tyr Glu Pro Ile Tyr Leu Gly Gly Val
    Phe Gln Leu Glu Lys Gly Asp Arg Leu Ser
    Thr Glu Val Asn Gln Pro Glu Tyr Leu Asp
    Leu Ala Glu Ser Gly Gln Val Tyr Phe Gly
    Ile Ile Ala Leu in which Ser in the 7th position from the N-terminus of the amino acid sequence is replaced by Gly.

8. A recombinant DNA consisting essentially of a base sequence of formula (5')-TCA GCT TCT CGG GCC CTG AGT GAC AAG       [I]
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3')

in which AGT, the 7th codon from the 5'-terminus of the base sequence, is replaced by GGT.

9. A recombinant DNA consisting essentially of a base sequence corresponding to an amino acid sequence of formula Ser Thr Glu Ser Met Ile Arg Asp Val Glu          [B]
    Leu Ala Glu Gly Pro Leu Pro Lys Lys Ala
    Gly Gly Pro Gln Gly Ser Lys Arg Cys Leu
    Cys Leu Ser Leu Phe Ser Phe Leu Leu Val
    Ala Gly Ala Thr Thr Leu Phe Cys Leu Leu
    His Phe Arg Val Ile Gly Pro Gln Glu Glu
    Glu Gln Ser Pro Asn Asn Leu His Leu Val
    Asn Pro Val Ala Gln Met Val Thr Leu Arg
    Ser Ala Ser Arg Ala Leu Ser Asp Lys Pro
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg
    Glu Thr Pro Glu Glu Ala Glu Pro Het Ala
    Trp Tyr Glu Pro Ile Tyr Leu Gly Gly Val
    Phe Gln Leu Glu Lys Gly Asp Arg Leu Ser
    Thr Glu Val Asn Gln Pro Glu Tyr Leu Asp
    Leu Ala Glu Ser Gly Gln Val Tyr Phe Gly
    Ile Ile Ala Leu in which Ser in the 87th position from the N-terminus of the amino acid sequence is replaced by Gly.

10. A recombinant DNA consisting essentially of a base sequence of formula (5')-AGC ACT GAG AGT ATG ATC CGG GAC GTC       [II]
GAG CTG GCG GAG GGG CCG CTC CCC AAG AAG
GCA GGG GGG CCC CAG GGC TCC AAG CGC TGC
CTC TGC CTC AGC CTC TTC TCT TTC CTG CTC
GTG GCT GGA GCC ACC ACG CTC TTC TGC CTG
CTG CAC TTC AGG GTG ATC GGC CCT CAG GAG
GAA GAG CAG TCC CCA AAC AAC CTC CAT CTA
GTC AAC CCT GTG GCC CAG ATG GTC ACC CTC
AGA TCA GCT TCT CGG GCC CTG AGT GAC AAG
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3')

wherein AGT, the 87th codon from the 5'-terminus of the base sequence, is replaced by GGT.

11. A vector into which the DNA of any one of claims 1, 2, 3, 4, 5, 7, 8, 9 or 10 is inserted.

12. The vector of claim 11 which is an expression vector.

13. The vector of claim 11 which can proliferate in *Escherichia coli.*

14. The vector of claim 11 which is an *Escherichia coli* plasmid.

15. A host selected from the group consisting of a microorganism, an animal cell and a plant cell which is transformed by the vector of any one of claims 12 to 14.

16. The host of claim 15 which is a microorganism.

17. The host of claim 16 which is *Escherichia coli.*

18. A process for producing a polypeptide consisting of a rabbit tumor necrosis factor, which comprises inserting a DNA comprising a base sequence encoding the rabbit tumor necrosis factor into an expression vector, transforming a host with the vector, cultivating the host, and collecting the resulting polypeptide consisting of the rabbit tumor necrosis factor.

19. A process for producing a DNA comprising a base sequence encoding a rabbit tumor necrosis factor, which comprises
   (1) cultivating rabbit macrophages together with induces,
   (2) separating a fraction containing a rabbit tumor necrosis factor mRNA from the macrophages,
   (3) preparing a single-stranded cDNA from the mRNA by using reverse transcriptase and then converting it to a double-stranded cDNA,
   (4) inserting the double-stranded cDNA into a plasmid vector,
   (5) introducing the recombinant plasmids into a host to transform it and construct a cDNA library,
   (6) cloning cDNA encoding the rabbit tumor necrosis factor from the library by using a differential hybridization method followed by mRNA hybridization translation assay.

20. The process of claim 19 which is for the production of a DNA comprising a base sequence corresponding to an amino acid sequence represented by the following formula:

Ser Ala Ser Arg Ala Leu Ser Asp Lys Pro           [A]
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg
    Glu Thr Pro Glu Glu Ala Glu Pro Met Ala
    Trp Tyr Glu Pro Ile Tyr Leu Gly Gly Val
    Phe Gln Leu Glu Lys Gly Asp Arg Leu Ser
    Thr Glu Val Asn Gln Pro Glu Tyr Leu Asp
    Leu Ala Glu Ser Gly Gln Val Tyr Phe Gly
    Ile Ile Ala Leu.

21. The process of claim 19 which is for the production of a DNA comprising a base sequence represented by the following formula:

[II]
    (5')-AGC ACT GAG AGT ATG ATC CGG GAC GTC
    GAG CTG GCG GAG GGG CCG CTC CCC AAG AAG
    GCA GGG GGG CCC CAG GGC TCC AAG CGC TGC
    CTC TGC CTC AGC CTC TTC TCT TTC CTG CTC
    GTG GCT GGA GCC ACC ACG CTC TTC TGC CTG
    CTG CAC TTC AGG GTG ATC GGC CCT CAG GAG
    GAA GAG CAG TCC CCA AAC AAC CTC CAT CTA
    GTC AAC CCT GTG GCC CAG ATG GTC ACC CTC
    AGA TCA GCT TCT CGG GCC CTG AGT GAC AAG
    CCT CTA GCC CAC GTA GTA GCA AAC CCG CAA
    GTG GAG GGC CAG CTC CAG TGG CTG AGC CAG
    CGT GCG AAC GCC CTG CTG GCC AAC GGC ATG
    AAG CTC ACG GAC AAC CAG CTG GTG GTG CCG
    GCC GAC GGG CTG TAC CTC ATC TAC TCC CAG
    GTT CTC TTC AGC GGT CAA GGC TGC CGC TCC
    TAC GTG CTC CTC ACT CAC ACT GTC AGC CGC
    TTC GCC GTC TCC TAC CCG AAC AAG GTC AAC
    CTC CTC TCT GCC ATC AAG AGC CCC TGC CAC
    CGG GAG ACC CCC GAG GAG GCT GAG CCC ATG
    GCC TGG TAC GAG CCC ATC TAC CTG GGC GGC
    GTC TTC CAG TTG GAG AAG GGT GAC CGG CTC
    AGC ACC GAG GTC AAC CAG CCT GAG TAC CTG
    GAC CTT GCC GAG TCC GGG CAG GTC TAC TTT
    GGG ATC ATT GCC CTG-(3').

22. The process of claim 19 which is for the production of a DNA comprising a base sequence corresponding to an amino acid sequence represented by the following formula:

Ser Thr Glu Ser Met Ile Arg Asp Val Glu          [B]
    Leu Ala Glu Gly Pro Leu Pro Lys Lys Ala
    Gly Gly Pro Gln Gly Ser Lys Arg Cys Leu
    Cys Leu Ser Leu Phe Ser Phe Leu Leu Val
    Ala Gly Ala Thr Thr Leu Phe Cys Leu Leu
    His Phe Arg Val Ile Gly Pro Gln Glu Glu
    Glu Gln Ser Pro Asn Asn Leu His Leu Val
    Asn Pro Val Ala Gln Met Val Thr Leu Arg
    Ser Ala Ser Arg Ala Leu Ser Asp Lys Pro
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg
    Glu Thr Pro Glu Glu Ala Glu Pro Met Ala
    Trp Tyr Glu Pro Ile Tyr Leu Gly Gly Val
    Phe Gln Leu Glu Lys Gly Asp Arg Leu Ser
    Thr Glu Val Asn Gln Pro Glu Tyr Leu Asp
    Leu Ala Glu Ser Gly Gln Val Tyr Phe Gly
    Ile Ile Ala Leu.

23. The process of claim 19 which is for the production of a DNA comprising a base sequence representd by the following formula:

[II]
    (5')-AGC ACT GAG AGT ATG ATC CGG GAC GTC
    GAG CTG GCG GAG GGG CCG CTC CCC AAG AAG
    GCA GGG GGG CCC CAG GGC TCC AAG CGC TGC
    CTC TGC CTC AGC CTC TTC TCT TTC CTG CTC
    GTG GCT GGA GCC ACC ACG CTC TTC TGC CTG
    CTG CAC TTC AGG GTG ATC GGC CCT CAG GAG
    GAA GAG CAG TCC CCA AAC AAC CTC CAT CTA
    GTC AAC CCT GTG GCC CAG ATG GTC ACC CTC
    AGA TCA GCT TCT CGG GCC CTG AGT GAC AAG
    CCT CTA GCC CAC GTA GTA GCA AAC CCG CAA
    GTG GAG GGC CAG CTC CAG TGG CTG AGC CAG
    CGT GCG AAC GCC CTG CTG GCC AAC GGC ATG
    AAG CTC ACG GAC AAC CAG CTG GTG GTG CCG
    GCC GAC GGG CTG TAC CTC ATC TAC TCC CAG
    GTT CTC TTC AGC GGT CAA GGC TGC CGC TCC
    TAC GTG CTC CTC ACT CAC ACT GTC AGC CGC
    TTC GCC GTC TCC TAC CCG AAC AAG GTC AAC
    CTC CTC TCT GCC ATC AAG AGC CCC TGC CAC
    CGG GAG ACC CCC GAG GAG GCT GAG CCC ATG
    GCC TGG TAC GAG CCC ATC TAC CTG GGC GGC
    GTC TTC CAG TTG GAG AAG GGT GAC CGG CTC
    AGC ACC GAG GTC AAC CAG CCT GAG TAC CTG
    GAC CTT GCC GAG TCC GGG CAG GTC TAC TTT
    GGG ATC ATT GCC CTG-(3').

24. The process of claim 18 wherein the vector is a plasmid which can proliferate in *Escherichia coli*.

25. The process of claim 18 wherein the host is *Escherichia coli*.

26. The process of claim 18 which is for the production of a polypeptide consisting of an amino acid sequence represented by the following formula:

Ser Ala Ser Arg Ala Leu Ser Asp Lys Pro           [A]
    Leu Ala His Val Val Ala Asn Pro Gln Val
    Glu Gly Gln Leu Gln Trp Leu Ser Gln Arg
    Ala Asn Ala Leu Leu Ala Asn Gly Met Lys
    Leu Thr Asp Asn Gln Leu Val Val Pro Ala
    Asp Gly Leu Tyr Leu Ile Tyr Ser Gln Val
    Leu Phe Ser Gly Gln Gly Cys Arg Ser Tyr
    Val Leu Leu Thr His Thr Val Ser Arg Phe
    Ala Val Ser Tyr Pro Asn Lys Val Asn Leu
    Leu Ser Ala Ile Lys Ser Pro Cys His Arg

-continued
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.

27. The process of claim 18 which is for the production of a polypeptide consisting of an amino acid sequence represented by the following formula:

Ser Thr Glu Ser Met Ile Arg Asp Val Glu [B]
Leu Ala Glu Gly Pro Leu Pro Lys Lys Ala
Gly Gly Pro Gln Gly Ser Lys Arg Cys Leu
Cys Leu Ser Leu Phe Ser Phe Leu Leu Val
Ala Gly Ala Thr Thr Leu Phe Cys Leu Leu
His Phe Arg Val Ile Gly Pro Gln Glu Glu
Glu Gln Ser Pro Asn Asn Leu His Leu Val
Asn Pro Val Ala Gln Met Val Thr Leu Arg
Ser Ala Ser Arg Ala Leu Ser Asp Lys Pro
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu.

28. A recombinant DNA consisting essentially of a base sequence a set forth in any one of claims 2, 3, 4, 5, 7, 8, 9 or 10 which has an initiation codon ATG at the 5'-terminus of the base sequence and/or a termination codon at the 3'-terminus of the base sequence.

29. A vector into which the DNA of claim 28 is inserted.

30. The vector of claim 29 which is an expression vector.

31. The process of claim 19 which is for the production of a DNA comprising a base sequence corresponding to an amino acid sequence of formula:

Ser Ala Ser Arg Ala Leu Ser Asp Lys Pro [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu in which Ser in the 7th position for the N-terminus of the amino acid sequence is replaced by Gly.

32. The process of claim 19 which is for the production of DNA comprising a base sequence of formula:

(5')-TCA GCT TCT CGG GCC CTG AGT GAC AAG [I]
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG

-continued
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3')

in which AGT, the 7th codon from the 5'-terminus of the base sequence, is replaced by GGT.

33. The process of claim 19 which is for the production of a DNA comprising a base sequence corresponding to an amino acid sequence of formula:

Ser Thr Glu Ser Met Ile Arg Asp Val Glu [B]
Leu Ala Glu Gly Pro Leu Pro Lys Lys Ala
Gly Gly Pro Gln Gly Ser Lys Arg Cys Leu
Cys Leu Ser Leu Phe Ser Phe Leu Leu Val
Ala Gly Ala Thr Thr Leu Phe Cys Leu Leu
His Phe Arg Val Ile Gly Pro Gln Glu Glu
Glu Gln Ser Pro Asn Asn Leu His Leu Val
Asn Pro Val Ala Gln Met Val Thr Leu Arg
Ser Ala Ser Arg Ala Leu Ser Asp Lys Pro
Leu Ala His Val Val Ala Asn Pro*Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Het Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu in which Ser in the 87th position from the N-terminus of the amino acid sequence is replaced by Gly.

34. The process of claim 19 which is for the production of a DNA comprising a base sequence of formula:

(5')-AGC ACT GAG AGT ATG ATC CGG GAC GTC [II]
GAG CTG GCG GAG GGG CCG CTC CCC AAG AAG
GCA GGG GGG CCC CAG GGC TCC AAG CGC TGC
CTC TGC CTC AGC CTC TTC TCT TTC CTG CTC
GTG GCT GGA GCC ACC ACG CTC TTC TGC CTG
CTG CAC TTC AGG GTG ATC GGC CCT CAG GAG
GAA GAG CAG TCC CCA AAC AAC CTC CAT CTA
GTC AAC CCT GTG GCC CAG ATG GTC ACC CTC
AGA TCA GCT TCT CGG GCC CTG AGT GAC AAG
CCT CTA GCC CAC GTA GTA GCA AAC CCG CAA
GTG GAG GGC CAG CTC CAG TGG CTG AGC CAG
CGT GCG AAC GCC CTG CTG GCC AAC GGC ATG
AAG CTC ACG GAC AAC CAG CTG GTG GTG CCG
GCC GAC GGG CTG TAC CTC ATC TAC TCC CAG
GTT CTC TTC AGC GGT CAA GGC TGC CGC TCC
TAC GTG CTC CTC ACT CAC ACT GTC AGC CGC
TTC GCC GTC TCC TAC CCG AAC AAG GTC AAC
CTC CTC TCT GCC ATC AAG AGC CCC TGC CAC
CGG GAG ACC CCC GAG GAG GCT GAG CCC ATG
GCC TGG TAC GAG CCC ATC TAC CTG GGC GGC
GTC TTC CAG TTG GAG AAG GGT GAC CGG CTC
AGC ACC GAG GTC AAC CAG CCT GAG TAC CTG
GAC CTT GCC GAG TCC GGG CAG GTC TAC TTT
GGG ATC ATT GCC CTG-(3')

in which AGT, the 87th codon from the 5'-terminus of the base sequence, is replaced by GGT.

35. The process of claim 18 which is for the production of a polypeptide consisting of an amino acid sequence of formula:

```
Ser Ala Ser Arg Ala Leu Ser Asp Lys Pro        [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu
``` in which Ser in the 7th position from the n-terminus of the amino acid sequence is replaced by Gly.

36. The process of claim 18 which is for the production of a polypeptide consisting of the amino acid sequence of formula:

```
Ser Thr Glu Ser Met Ile Arg Asp Val Glu        [B]
Leu Ala Glu Gly Pro Leu Pro Lys Lys Ala
Gly Gly Pro Gln Gly Ser Lys Arg Cys Leu
Cys Leu Ser Leu Phe Ser Phe Leu Leu Val
Ala Gly Ala Thr Thr Leu Phe Cys Leu Leu
His Phe Arg Val Ile Gly Pro Gln Glu Glu
Glu Gln Ser Pro Asn Asn Leu His Leu Val
Asn Pro Val Ala Gln Met Val Thr Leu Arg
Ser Ala Ser Arg Ala Leu Ser Asp Lys Pro
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Het Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu
``` in which Ser in the 87th position from the N-terminus of the amino acid sequence is replaced by Gly.

37. A process for producing a polypeptide consisting of an amino acid sequence of formula:

```
Ser Ala Ser Arg Ala Leu Ser Asp Lys Pro        [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu
``` in which Ser in the 7th position from the N-terminus of the amino acid sequence is replaced by Gly, which comprises inserting a DNA as defined in claim 7 into an expression vector, transforming a host with the vector, cultivating the host and collecting the polypeptide.

38. The process of claim 18 which is for the production of a polypeptide consisting of an amino acid sequence of the formula

```
Ser Ala Ser Arg Ala Leu Ser Asp Lys Pro        [A]
Leu Ala His Val Val Ala Asn Pro Gln Val
Glu Gly Gln Leu Gln Trp Leu Ser Gln Arg
Ala Asn Ala Leu Leu Ala Asn Gly Met Lys
Leu Thr Asp Asn Gln Leu Val Val Pro Ala
Asp Gly Leu Tyr Leu Ile Tyr Ser Gln Val
Leu Phe Ser Gly Gln Gly Cys Arg Ser Tyr
Val Leu Leu Thr His Thr Val Ser Arg Phe
Ala Val Ser Tyr Pro Asn Lys Val Asn Leu
Leu Ser Ala Ile Lys Ser Pro Cys His Arg
Glu Thr Pro Glu Glu Ala Glu Pro Met Ala
Trp Tyr Glu Pro Ile Tyr Leu Gly Gly Val
Phe Gln Leu Glu Lys Gly Asp Arg Leu Ser
Thr Glu Val Asn Gln Pro Glu Tyr Leu Asp
Leu Ala Glu Ser Gly Gln Val Tyr Phe Gly
Ile Ile Ala Leu
``` which has methionine at the N-terminus of the amino acid sequence.

* * * * *